US00PP32566P2

(12) United States Plant Patent
Losert

(10) Patent No.: US PP32,566 P2
(45) Date of Patent: Dec. 1, 2020

(54) ***CALIBRACHOA* PLANT NAMED 'KLECA19487'**

(50) Latin Name: ***Calibrachoa* sp.**
Varietal Denomination: KLECA19487

(71) Applicant: Klemm+Sohn GmbH & Co. KG, Stuttgart (DE)

(72) Inventor: Dominik Losert, Aspach (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/867,645

(22) Filed: May 6, 2020

(51) Int. Cl.
*A01H 6/82* (2018.01)
*A01H 5/02* (2018.01)

(52) U.S. Cl.
USPC ..... Plt./439

(58) Field of Classification Search
USPC ..... Plt./439
See application file for complete search history.

*Primary Examiner* — Annette H Para
(74) *Attorney, Agent, or Firm* — Weatherly IP Solutions, LLC; James Weatherly

(57) ABSTRACT

A new *Calibrachoa* plant particularly distinguished by having a medium blue violet flower color and a compact, mounding form with a semi-trailing plant habit, is disclosed.

1 Drawing Sheet

Genus and species: *Calibrachoa* sp.
Variety denomination: 'KLECA19487'.

BACKGROUND OF THE NEW PLANT

The present invention comprises a new and distinct variety of *Calibrachoa*, botanically known as *Calibrachoa* sp, and hereinafter referred to by the variety name 'KLECA19487'. 'KLECA19487' originated from a controlled-cross between the proprietary female *Calibrachoa* variety 'CA-2015-6490' (unpatented) and the male *Calibrachoa* variety 'Duealkomidbu' (U.S. Plant Pat. No. 25,487).

In August 2015, two *Calibrachoa* parental lines, 'CA-2015-6490' and the male *Calibrachoa* variety 'Duealkomidbu' were crossed via a controlled cross in Stuttgart, Germany and seeds were obtained. The seeds were sown and plants were grown for evaluation. A plant line was selected in May 2016 and subsequently named 'KLECA19487'. In June 2016, 'KLECA19487' was first vegetatively propagated by tip cuttings. 'KLECA19487' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Medium blue violet flower color; and
2. Broad to very broad flower size.

DESCRIPTION OF THE PHOTOGRAPH

This new *Calibrachoa* plant is illustrated by the accompanying photograph which shows a close-up of the whole plant. The photograph is of a 13 week old plant grown in in Stuttgart, Germany in July 2018. The colors shown are as true as can be reasonably obtained by conventional photographic procedures.

DESCRIPTION OF THE NEW VARIETY

The following detailed descriptions set forth the distinctive characteristics of 'KLECA19487'. The data which define these characteristics were collected from asexual reproductions carried out in Stuttgart, Germany. Data was collected on 18-week old plants after potting grown in Stuttgart, Germany March 2020. Color references are to The R.H.S. Colour Chart of The Royal Horticultural Society of London (R.H.S.), 5$^{th}$ edition (2007).

Classification:
- *Family.*—Solanaceae.
- *Species.*—*Calibrachoa* sp.
- *Common name.*—*Calibrachoa.*

Parentage:
- *Female.*—Proprietary *Calibrachoa* line 'CA-2015-6490'.
- *Male.*—*Calibrachoa* line 'Duealkomidbu' (U.S. Plant Pat. No. 25,487).

Plant description:
- *Life cycle.*—Annual.
- *Form.*—Short lived subshrub.
- *Habit.*—Upright.
- *Height (from soil line to top of foliage).*—17.7 cm.
- *Spread.*—29.4 cm.

Propagation:
- *Type cuttings.*—Tip cuttings.
- *Time to produce a rooted cutting.*—3 weeks.

Stems:
- *Stem color.*—RHS 144C.
- *Pubescence.*—Yes.
- *Pubescence color.*—RHS 155A.
- *Stem diameter.*—0.3 cm.
- *Stem length.*—27.7 cm. From soil line to first node: 1.7 cm. Internode length: 1.9 cm.

Leaves:
- *Arrangement.*—Alternate.
- *Shape.*—Elliptic.
- *Apex.*—Broadly acute.

*Base*.—Attentuate.
*Margin*.—Ciliate.
*Surface* (*both upper and lower*).—Puberulent.
*Surface pubescence*.—Present.
*Pubescent color*.—RHS 155A.
*Venation*.—Pinnate.
*Venation color*.—Upper surface: RHS 144B. Lower surface: RHS 145B.
*Length*.—2.4 cm to 3.7 cm.
*Width*.—1.1 cm to 2.0 cm.
*Color*.—Upper surface: RHS N137C. Lower surface: RHS 138B.
*Fragrance*.—Absent.

Flowers:
*Flowering habit*.—Single.
*Flower type*.—Single.
*Flowering requirements*.—Continuous flowering from spring through autumn and all the time/year-around in greenhouse environment.
*Duration of flowers*.—6 days.
*Corolla*.—Smooth.
*Shape*.—Funnel-shaped.
*Fragrance*.—Absent.
*Number of flowers per plant*.—25.

Flower buds (before opening):
*Surface*.—Smooth, pubescent.
*Texture*.—Pubescence on the petal ribs.
*Length*.—2.7 cm.
*Diameter*.—1.1 cm.
*Shape*.—Trumpet.
*Color*.—RHS 5A (throat) and RHS 83A (limbs).
*Typical number per plant*.—3.

Petiole:
*Length*.—Sessile.
*Diameter*.—Sessile.

Peduncle:
*Length*.—1.6 cm.
*Diameter*.—0.1 cm.
*Color*.—RHS 144A.
*Texture*.—Puberulent.
*Anthocyanin color*.—Absent.

Flower description:
*Flower depth*.—1.9 cm.
*Flower tube length*.—1.3 cm.
*Flower tube diameter*.—0.8 cm.
*Flower diameter*.—3.8 cm.
*Flower throat diameter*.—1.2 cm.
*Pedicel color*.—RHS 144A.
*Calyx*.—Funnel-shaped.

Sepals:
*Quantity*.—5.
*Shape*.—Lanceolate.
*Texture*.—Pubescence.
*Apex*.—Narrowly acute.
*Margin*.—Ciliate.
*Length*.—1.6 cm.
*Diameter*.—0.4 cm.
*Sepal color*.—Upper surface: RHS 137C. Lower surface: RHS 138A.

Petals:
*Shape*.—Obcordate.
*Quantity*.—5.
*Length*.—1.5 cm.
*Apex*.—Emarginate.
*Margin*.—Entire.
*Base*.—Fused into the tube.
*Lobe length*.—1.4 cm.
*Lobe width*.—1.3 cm.
*Color*.—Marking: Partially star shaped. Recent main lobe color: Upper surface: RHS 83B. Lower surface: RHS 84A. Old main lobe: Upper surface: RHS N87B. Lower surface: RHS 84A. Recent transition lobe: Upper surface: RHS N92C. Lower surface: RHS 79A. Old transition lobe: Upper surface: RHS 79B. Lower surface: RHS 86A. Recent vein lobe: Upper surface: RHS N92C. Lower surface: RHS N77A. Old vein lobe: Upper surface: RHS 79A. Lower surface: RHS 79A.
*Transition lobe color size*.—Medium.
*Vein corolla tube color*.—Inner: RHS N186A. Outer: RHS N187A.
*Corolla tube color*.—Inner: RHS 1A. Outer: 1C.
*Texture*.—Upper surface: Absent. Lower surface: Light pubescence, dense pubescence along venation.
*Fragrance*.—Absent.

Reproductive organs:
*Stamen number*.—5.
*Stamen color*.—Anther color: RHS 9A. Anther spabe: Bilobed, ovoid. Anther length: 0.1 cm. Filament length: 1.0 cm. Filament color: RHS 154C. Pollen color: RHS 8B.
*Ovary*.—Placenta arrangement: Ovate. Pistil number: 1. Pistil length: 0.8 cm. Stigma color: RHS 149A. Stigma shape: Funnel. Style length: 0.6 cm. Style color: RHS 150B.

Fruit/seed set: None observed.

Disease/insect resistance: No pests and disease were observed.

COMPARISON WITH PARENTAL LINES AND KNOWN VARIETY

'KLECA19487' is distinguished from its parents as described in Table 1:

TABLE 1

Comparison with Parental Lines

| Trait | Variety 'KLECA19487' | Female parent 'CA-2015-6490' | Male Parent 'Duealkomidbu' |
|---|---|---|---|
| Flower size | Broad to very broad | Medium to broad | Medium to broad |
| Lobe color | RHS 83B | RHS 81A | RHS 81A |

'KLECA19487' is most similar to the *Calibrachoa* plant named 'KLECA17399' (not patented). Differences between the two varieties are described in Table 2:

TABLE 2

Comparison with Similar Variety

| Trait | Variety 'KLECA19487' | Commercial line 'KLECA17399' |
|---|---|---|
| Flower size | Broad to very broad | Medium to broad |
| Area of main color at transition to corolla tube | Small | Medium |

I claim:

1. A new and distinct variety of *Calibrachoa* plant named 'KLECA19487' as shown and described herein.

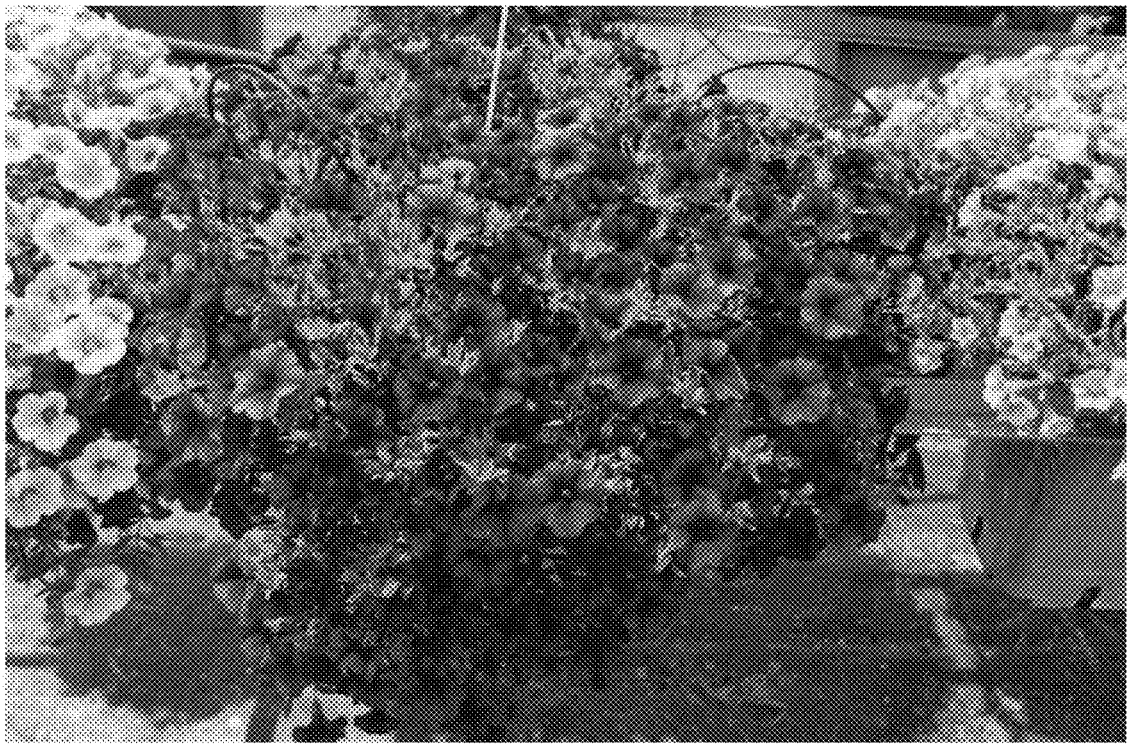

* * * * *